United States Patent [19]

Aviron-Violet et al.

[11] 4,237,072

[45] Dec. 2, 1980

[54] PREPARATION OF OPTICALLY ACTIVE CITRONELLAL

[75] Inventors: Paul Aviron-Violet, Saint-Genis Laval; Tuan-Phat Dang, Lyon, both of France

[73] Assignee: Rhone-Poulenc Industries, Paris, France

[21] Appl. No.: 920,981

[22] Filed: Jun. 30, 1978

[30] Foreign Application Priority Data

Jul. 4, 1977 [FR] France ................................ 77 21377

[51] Int. Cl.³ ............................................. C07C 47/20
[52] U.S. Cl. ..:............................................... 568/459
[58] Field of Search .................................... 260/601 R

[56] References Cited

U.S. PATENT DOCUMENTS

| 3,489,786 | 1/1970 | Dewhirst | 260/601 R |
|---|---|---|---|
| 3,860,657 | 1/1975 | Easter, Jr., et al. | 260/601 R |
| 3,971,830 | 7/1976 | Gradeff | 260/601 R |
| 4,029,709 | 6/1977 | DeSimone et al. | 260/601 R |

OTHER PUBLICATIONS

Leffingwell et al., Cosmetics & Perfumery 89(1974) pp. 69–78.
O'Donnell et al., Aust. J. Chem., 19 (1966) pp. 525–528.

*Primary Examiner*—Werren B. Lone
*Attorney, Agent, or Firm*—Burns, Doane, Swecker & Mathis

[57] ABSTRACT

Neral or geranial are hydrogenated into optically active citronellal in the presence of a catalytic complex comprising a rhodium derivative and a chiral phosphine.

18 Claims, No Drawings

PREPARATION OF OPTICALLY ACTIVE CITRONELLAL

BACKGROUND OF THE INVENTION

1. Field of the Invention

The present invention relates to a process for the preparation of optically active citronellal, which is also referred to as chiral citronellal, by the asymmetric hydrogenation of neral [E-3,7-dimethyloctadien-2,6-al] or geranial [Z-3,7-dimethyloctadien-2,6-al] which are achiral isomeric constituents of citral.

2. Description of the Prior Art

Chiral citronellal is a valuable intermediate in organic synthesis; in particular, d-citronellal is used for the preparation of (−) (1S)-menthol, hereafter simply l-menthol, by a process which employs the cyclization of d-citronellal into (−) (1S)-isopulegol under the influence of a proton catalyst, or by a thermal route, followed by the hydrogenation of the isopulegol into l-menthol [cf., J. C. Leffingwell and R. E. Shackelford, *Cosmetics and Perfumery*, 89, 70–78 (1974)].

The d-citronellal used for the synthesis of l-menthol is obtained from various essential oils largely comprised of d-citronellal and, in particular, from citronella oil. The use of chiral citronellal of natural origin is not entirely satisfactory insofar as, because of the fluctuation in the prices of natural products, it periodically happens that the price of d-citronellal is higher than that of natural menthol. It is therefore of importance to industry to have available a source of chiral citronellal which has a relatively stable price and leads to a synthetic l-menthol having a lower cost price than that of natural menthol.

The synthetic achiral citronellal obtained via the hydrogenation of citral [a mixture of neral and geranial] could constitute a valuable source of chiral citronellal and especially of d-citronellal; however, no industrial process exists for resolving racemic citronellal into its enantiomers, with the result that industry does not have any process available which makes it possible to obtain chiral citronellals by a synthetic route.

SUMMARY OF THE INVENTION

Accordingly, a primary object of the present invention is to provide a process for the preparation of optically active citronellal, by hydrogenating neral or geranial in the presence of a catalyst comprising a complex which is soluble in the reaction medium and which is formed from a rhodium derivative and a chiral phosphine.

DETAILED DESCRIPTION OF THE INVENTION

The term chiral phosphine denotes a phosphine or diphosphine in which at least one of the organic radicals bonded to the phosphorous atom contains at least one chiral carbon atom, and/or in which at least one of the phosphorus atoms is chiral.

The soluble complex of the rhodium derivative and the chiral phosphine can be prepared for immediate use or formed "in situ" under the reaction conditions by merely employing the constituents of the complex. The latter procedure, which has the advantage of simplicity, is generally preferred.

Rhodium derivatives containing radicals of a diverse nature are used as rhodium derivatives which are suitable for carrying out the process according to the invention. They can be rhodium salts of mineral or organic acids or rhodium complexes in which the ligands can be replaced by the chiral phosphine. It is possible to use, for example, rhodium halides such as hydrated rhodium trichloride, and complexes of rhodium with olefins, these complexes having the general formula:

$$[RhX(L)_x]_2 \qquad (I)$$

in which X represents a halogen atom, for example, chlorine or bromine, x is an integer from 1 to 4 and L is an olefin or an aliphatic or cycloaliphatic diolefin, such as ethylene, propylene, butene, isobutene, butadiene, hexa-1,5-diene, hepta-1,4-diene, octa-1,5-diene, isoprene, cyclohexa-1,3-diene or cycloocta-1,5-diene; examples of such complexes which may be mentioned are $\mu,\mu'$-dichloro-bis-(cyclohexa-1,3-dienerhodium), $\mu,\mu'$-dichloro-bis-(cycloocta-1,5-dienerhodium) and $\mu,\mu'$-dichloro-bis-(diethylenerhodium); it is also possible to use rhodium carbonyl complexes and their derivatives such as those corresponding to the general formula:

$$RhH(CO)(L_1)_3$$

in which $L_1$ represents a mono- or poly-dentate ligand and especially an achiral phosphine of the general formula:

$$P(R)_3$$

in which R represents an achiral alkyl, cycloalkyl or aryl radical having from 1 to 10 carbon atoms, such as the methyl, ethyl, propyl, butyl, pentyl, hexyl, octyl, cyclohexyl, phenyl or toluyl radicals. $L_1$ is preferably triphenylphosphine. The various rhodium carbonyls, and especially tetrarhodium dodecacarbonyl and hexarhodium hexadecacarbonyl, are preferably used from among the above-mentioned rhodium derivatives. Rhodium complexes in the cationic form can also be used.

Both monophosphines and diphosphines can be used as the chiral phosphine which is suitable for carrying out the invention. Diphenylmenthylphosphine, phenyldimenthylphosphine and trimenthylphosphine are mentioned as examples of chiral monophosphines. However, it is preferred to use chiral diphosphines of the general formula:

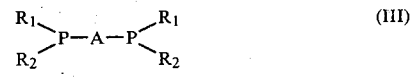

in which: $R_1$ and $R_2$, which are identical or different, represent hydrocarbon radicals having from 1 to 15 carbon atoms and A represents a valence bond or a divalent organic radical which is optionally substituted by one or more inert functional groups, at least one of the radicals $R_1$, $R_2$ and A being chiral.

More specifically, $R_1$ and $R_2$, which are preferably identical, represent alkyl radicals having from 1 to 10 carbon atoms [methyl, ethyl, isobutyl, sec.-butyl, sec.-pentyl or 2-ethylhexyl radicals], cycloalkyl radicals having from 4 to 8 cyclic carbon atoms [cyclobutyl, 1-methylcyclobutyl, cyclohexyl, 1-methylcyclohexyl or 2-methylcyclohexyl radicals], or aryl or alkylaryl radicals [phenyl, naphthyl or toluyl radicals]. A represents:

a linear or branched alkylene radical having from 1 to 10 carbon atoms, a cycloalkylene radical which has from 3 to 7 cyclic carbon atoms and is optionally substituted by 1 to 3 alkyl groups having from 1 to 4 carbon atoms, an arylene radical or a divalent polycyclic radical, these radicals being optionally substituted by 1 or more inert functional groups and, in particular, by 1 to 3 alkoxy groups having from 1 to 4 carbon atoms, a divalent heterocyclic group [pyridylene or 1,3-dioxacyclopent-4,5-ylene] having 1 or 2 hetero-atoms such as oxygen and/or nitrogen, a linkage consisting of 1 or more divalent alkylene and/or cycloalkylene and/or heterocyclic and/or polycyclic radicals such as those defined previously, or a linkage consisting of alkylene groups such as those defined previously and tertiary amino groups which can optionally be bonded directly to the phosphorus atoms via the nitrogen atom.

Methylene, ethylene, propylene and 2-ethylpropylene radicals may be mentioned as examples of alkylene radicals; A can also represent a cyclobutylene, cyclohex-1,4-ylene or 2-methylcyclohex-1,4-ylene radical, or ortho- or p-phenylene radical or a 2,3-dimethoxybut-1,4-ylene radical.

As examples of divalent chiral radicals A formed by a linkage consisting of alkylene and cycloalkylene or heterocyclic, polycyclic or amino radicals, there are mentioned those of the formulae

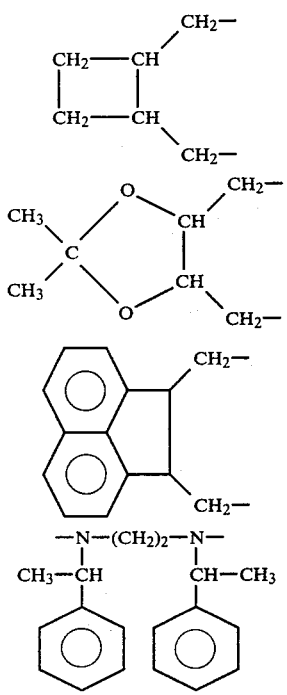

Among the chiral diphosphines which can be used in the process according to the invention, the following are mentioned strictly as illustrative: 1,2-bis-(diphenylphosphinomethyl)-cyclobutane (DPCB), 1,2-bis-(dimethylphosphinomethyl)-cyclobutane, 1,2-bis-(di-n-butylphosphinomethyl)-cyclobutane, 1,2-bis-(dioctylphosphinomethyl)-cyclobutane, 1,2-bis(ditolylphosphinomethyl)-cyclobutane, 1,2-bis-(dinaphthylphosphinomethyl)-cyclobutane, 1,2-bis-(ethylhexylphosphinomethyl)-cyclobutane, 1,2-bis-(diphenylphosphinomethyl)-cyclopentane, 1,2-bis-(diphenylphosphinomethyl)-cyclohexane, 4,5-bis-(dimethylphosphinomethyl)-2,2-dimethyl-1,3-dioxolane, 4,5-bis-(diphenylphosphinomethyl)-2,2-dimethyl-1,3-dioxolane (DIOP), 4,5-bis-(ditolylphosphinomethyl)-2,2-dimethyl-1,3-dioxolane, 1,2-bis-(dimethylphosphinomethyl)-acenaphthene, 1,2-bis-(dibutylphosphinomethyl)-acenaphthene, 1,2-bis-(diphenylphosphinomethyl)-acenaphthene (DPA), 1,2-bis-(ditolylphosphinomethyl)-acenaphthene, 1,4-bis-(diphenylphosphino)-2,3-dimethoxybutane (DDB), tetramenthyl diphosphine and bis-(N,N'-diphenylphosphino)-bis-[N,N'-(1-phenylethyl)]-1,4-diazabutane.

From among those phosphines previously mentioned, the 1,2-bis-(diarylphosphinomethyl)-cyclobutanes described in French Pat. No. 73/18,319, hereby expressly incorporated by reference, are preferably used.

Methylcyclohexyl-ortho-methoxyphenylphosphine, methylcyclohexylphenylphosphine and benzylphenylmethylphosphine are mentioned as examples of phosphines having chiral phosphorus atoms.

The complexes derived from $Rh_4(CO)_{12}$ or $Rh_6(CO)_{16}$ and from 1,2-bis-(diarylphosphinomethyl)-cyclobutanes are very particularly suitable for the asymmetric hydrogenation of neral and geranial to give enantiomers of citronellal, because they simultaneously provide a high hydrogenation rate, a good selectivity with respect to citronellal and a good optical purity.

The amount of rhodium derivative employed in the process of the invention, and expressed in gram atoms of metal per mol of diene aldehyde to be hydrogenated, can vary over wide limits. Whether the preformed complex is used or whether the derivative which is capable of generating this complex under the reaction conditions is used, the amount can be selected such that the number of gram atoms of rhodium per mol of aldehyde is between $1 \times 10^{-4}$ and $1 \times 10^{-1}$.

When the rhodium derivative/chiral phosphine complex is prepared "in situ", the amount of phosphine employed in the process depends on the nature of the phosphine and on that of the rhodium derivative. This amount, expressed as the number of gram atoms of phosphorus per gram atom of rhodium, is such that this ratio can vary between 0.5 and 10; the ratio of P/Rh is preferably between 1 and 6. However, ratios of P/Rh which are greater than 10 could be employed without departing from the scope of the present invention, but no particular advantage would be gained thereby.

The temperature at which the hydrogenation is carried out is not critical and can also vary over wide limits. It is generally between 0° and 150° C. and preferably between 10° and 100° C. The same applies to the hydrogen pressure which can vary between 0.1 and 100 bars, and preferably between 0.5 and 50 bars.

Although the diene aldehyde which is subjected to the asymmetric hydrogenation should preferably be as pure as possible, that is to say, virtually free from its isomer, it is possible to employ neral containing up to 15% of geranial, and vice versa.

Similarly, it is preferable to use a chiral phosphine which does not contain its enantiomer, although it is possible to carry out the reaction with a chiral phosphine containing less than 15% of its enantiomer.

The asymmetric hydrogenation of neral or geranial is preferably carried out in a solvent which is inert towards the aldehyde and the catalyst. Hydrocarbons [hexane, heptane, cyclohexane, benzene and toluene], alcohols [methanol and ethanol] and nitriles [acetonitrile and benzonitrile] are mentioned as examples of solvents.

In order to further illustrate the present invention and the advantages thereof, the following specific examples are given, it being understood that the same are intended only as illustrative and in nowise limitative. In these examples, the term optical purity OP will denote the ratio of the rotatory power $[\alpha_1]_D$ of the product obtained by the process to the rotatory power $[\alpha]_D$ of the pure product measured under the same conditions, this ratio being multiplied by 100; that is to say OP in % = $([\alpha_1]_D/[\alpha]_D) \cdot 100$ The term optical yield denotes the value of the optical purity of the product which would be obtained by using an optically pure phosphine.

EXAMPLE 1

18.2 mg of $Rh_6(CO)_{16}$ ($1.02 \times 10^{-4}$ g atoms of Rh) and 67.5 mg of (+)-(DPCB), that is to say, 0.15 millimol, were introduced into a 50 cm$^3$ glass round-bottomed flask equipped with a dip-tube gas inlet, a thermometer, a magnetic stirrer and a glass stopper which makes it possible to add reagents or withdraw samples of the reaction mixture by means of a syringe, the apparatus was then purged with nitrogen and 20 cm$^3$ of toluene were injected. The contents of the flask were stirred for 1 hour under a nitrogen atmosphere and 1.79 g [that is to say 11.77 millimols] of geranial containing 5% of neral were then added. The apparatus was purged with hydrogen and the contents of the flask were then kept under a hydrogen pressure of 1 bar for 4 hours at 25° C. The reaction was stopped and the reaction mixture was analyzed by gas phase chromatography; the degree of conversion of the geranial was 100% and the yield of citronellal was 99%. The solvent was evaporated off and the residue was then distilled under reduced pressure. 1.28 g of l-citronellal having a rotatory power $[\alpha]_D^{25}$ of −8.76° (measured on a solution in hexane containing 6 g per 100 cm$^3$) and $[\alpha]_D^{25}$ of −9.1° (measured in the absence of solvent) are thus collected. The rotatory power $[\alpha]_D^{25}$ of pure l-citronellal, measured on a solution in cyclohexane containing 6 g/100 cm$^3$, was −15.6°. On the basis of this value, the OP of the product obtained was 56%. The rotary power $[\alpha]_D^{25}$ of pure l-citronellal (determination without solvent) was −16° [cf. Donell et al., *Australian J. Chem.*, 19, 525 (1966)].

EXAMPLE 2

The procedure of Example 1 was followed, using the following amounts:

| | |
|---|---|
| $Rh_6(CO)_{16}$ | 17.8 mg |
| (+)-DPCB | 68 mg |
| Neral containing 12% of geranial | 11 g |
| The reaction time was 10 hours. | |
| Degree of conversion | 100% |
| Yield of citronellal | 99% |

After distillation, 9.6 g of citronnellal were collected, for which $[\alpha]_D^{25} = +10.15°$ (solution in hexane containing 6 g/100 cm$^3$), this being an optical purity of 65%.

EXAMPLES 3 AND 4

The procedure of Example 1 was followed, the (+)-DPCB being replaced by (+)-DIOP. The ratio of geranial/Rh was 120 and ratios of P/Rh of 4 and 6 were used successively.

Under these conditions, the following results were obtained:

| Example | P/Rh | Duration in Hours | Degree of Conversion % | Y (1) % | OP | $[\alpha]_D^{25}$ |
|---|---|---|---|---|---|---|
| 3 | 4 | 20 | 97 | 98 | 51 | + 8.2° (2) |
| 4 | 6 | 20 | 98 | 99 | 50 | + 8° (2) |

(1) yield of citronellal relative to the geranial converted
(2) measured on the pure product

EXAMPLE 5

The procedure of Example 1 was followed, (+)-DPCB being replaced by (−)-DPCB. The ratio of the number of mols of geranial (G) to the number of gram atoms of rhodium (G/Rh) was equal to 123 and the ratio of P/Rh was equal to 4. The (−)-DPCB had an optical purity of 95.5%.

The reaction time was 18 hours, the degree of conversion of the geranial was 99% and the yield of citronellal is 99%. The optical purity of the d-citronellal obtained was 49% ($[\alpha]_D^{25} = +7.7°$, solution in hexane containing 6 g/100 cm$^3$). If the purity of the phosphine was taken into account, the optical yield increased to 52%.

EXAMPLE 6

The procedure of Example 5 was followed, the geranial being replaced by neral and the other conditions being otherwise identical. The following results were obtained:

| | |
|---|---|
| Hydrogenation time | 18 hours |
| Degree of conversion of neral | 100% |
| Y of citronellal | 88% |
| $[\alpha]_D^{25}$ in hexane containing 6 g/100 cm$^3$ | −9° |
| Optical purity | 57% |

EXAMPLE 7

The reaction was carried out in accordance with the method of operation of Example 1 and under the same pressure and temperature conditions, $Rh_6(CO)_{16}$ being replaced by $Rh_4(CO)_{12}$. The ratio of P/Rh is 3 and the ratio of G/Rh was 120. The results were as follows:

| | |
|---|---|
| Duration | 3 hours 30 minutes |
| DC | 100% |
| Y of citronellal | 99% |
| $[\alpha]_D^{25}$ in hexane | −8.1° |
| OP | 52% |

EXAMPLE 8

The procedure of Example 7 was followed, the geranial being replaced by neral. (The ratio of N/Rh was 140.) The following results were obtained:

| | |
|---|---|
| Duration | 2 hours 45 minutes |
| DC of neral | 100% |
| Y of citronellal | 100% |
| $[\alpha]_D^{25}$ measured in hexane | +10.3° |
| OP | 66% |

EXAMPLE 9

The procedure of Example 1 was followed, bringing the ratio of N/Rh to 750 instead of 115 and the ratio of P/Rh to 2. The following results were obtained:

| Duration | 6 hours 40 minutes |
| --- | --- |
| DC of neral | 100% |
| Y of citronellal | 100% |
| $[\alpha]_D^{25}$ measured in hexane | +10.9° |
| OP | 70% |

The neral used contained 7% of geranial.

EXAMPLES 10 to 18

The reaction was carried out in accordance with the method of operation and the temperature and pressure conditions of Example 1, varying the nature of the aldehyde, the chiral phosphine and the rhodium derivative. The other conditions and the results obtained are included in the following table:

| Example | PHOSPHINE | Rhodium Derivative | ENAL | P/Rh | ENAL/Rh | Duration in hours | DC of ENAL % | Y % | $[\alpha]_D^{25°}$ | OP % |
| --- | --- | --- | --- | --- | --- | --- | --- | --- | --- | --- |
| 10 | (+)-DPCB | RhH(CO) (P$\phi_3$)$_3$ [1] | geranial | 6 | 123 | 70 | 81 | 99 | −7.6[2] | 58 |
| 11 | (−)-DIOP | " | " | 6 | 134 | 108 | 83 | 100 | +7.3[3] | 54 |
| 12 | (−)-DPCB | " | " | 2 | 149 | 29 | 95 | 100 | +8.7[3] | 54 |
| 13 | " | " | neral | 6 | 108 | 73 | 93 | 98 | −10[3] | 67 |
| 14 | " | " | geranial | 2 | 570 | 40 | 96 | 100 | +8.4[3] | 55 |
| 15 | " | " | " | 2 | 2,100 | 65 | 95 | 98 | +9[2] | 58 |
| 16 | (−)DDB | " | " | 2.6 | 114 | 28 | 68 | 98 | +1.9[3] | 19.5 |
| 17 | " | " | neral | 2 | 105 | 65 | 67 | 98 | −2.1[3] | 20 |
| 18 | (+)-DPA | " | geranial | 2 | 136 | 22 | 40 | 98 | −1.7[3] | 27 |

[1] in the formula RhH(CO) (P$\phi_3$)$_3$, P$\phi_3$ denotes triphenylphosphine
[2] measured on a solution in hexane containing 6 g/100 cm$^3$
[3] measured on the product obtained

EXAMPLE 19

A 35 cm$^3$ glass ampoule containing 10 cm$^3$ of toluene, 18.3 mg of (−)-DPCB, 91.9 mg of RhH(CO) (P$\phi_3$)$_3$ and 1.91 g of geranial were introduced into a 125 cm$^3$ stainless steel autoclave equipped with a system for agitation by shaking. The autoclave was closed and hydrogen was introduced up to a pressure of 25 bars. These conditions were maintained for 17 hours, the autoclave was then degassed and the contents of the ampoule were treated and analyzed as in Example 1.

The degree of conversion of the geranial was 69%, the yield of citronellal relative to the geranial converted was 99% and the optical purity was 60% (rotatory power $[\alpha]_D^{25} = +6.6°$ measured on the pure product).

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A process for the preparation of optically active citronellal by the asymmetrical hydrogenation of neral or geranial, comprising treating neral or geranial with hydrogen in a liquid reaction medium in the presence of an amount sufficient to catalyze the conversion of said neral or geranial to said optically active citronellal of an optically active catalyst consisting essentially of a complex which is soluble in the reaction medium and formed from a rhodium derivative and a chiral phosphine under a hydrogen pressure and at a temperature sufficient for hydrogenating the neral or geranial into the citronellal and for a period of time sufficient to convert substantially all of the neral or geranial into the citronellal.

2. The process as defined by claim 1, wherein the complex of rhodium and of the chiral phosphine is pre-prepared.

3. The process as defined in claim 1, wherein the complex of rhodium and of the chiral phosphine is formed "in situ" from a rhodium derivative and a chiral phosphine.

4. The process as defined by claim 3, wherein the rhodium derivative is a salt of a mineral or organic acid or a complex of rhodium with an achiral ligand.

5. The process as defined by claim 4, wherein the rhodium derivative is rhodium trichloride.

6. The process as defined by claim 4, wherein the rhodium complex has the general formula:

$$[RhX(L)_x]_2 \tag{I}$$

in which X represents a halogen atom, x is an integer from 1 to 4 and L represents a mono- or di-olefin.

7. The process as defined by claim 6, wherein the rhodium complex is $\mu,\mu'$-dichloro-bis-(cycloocta-1,5-dienerhodium).

8. The process as defined by claim 4, wherein the rhodium complex has the general formula:

$$RhH(CO)(PR_3)_3 \tag{II}$$

in which R represents an achiral alkyl, cycloalkyl or aryl radical having from 1 to 10 carbon atoms.

9. The process as defined by claim 8, wherein the rhodium complex has the formula RhH(CO)[P(C$_6$H$_5$)$_3$]$_3$.

10. The process as defined by claim 4, wherein the rhodium complex is a rhodium carbonyl selected from the group consisting of tetrarhodium dodecacarbonyl and hexarhodium hexadecacarbonyl.

11. The process as defined by claim 1, wherein the chiral phosphine contains at least one chiral carbon atom and/or at least one chiral phosphorus atom.

12. The process as defined by claim 11, wherein the chiral phosphine is a diphosphine of the general formula:

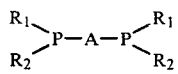

in which: $R_1$ and $R_2$, which are identical or different, represent hydrocarbon radicals having from 1 to 15 carbon atoms and A represents a valence bond or a divalent organic radical which is optionally substituted by one or more inert functional groups, at least one of the radicals $R_1$, $R_2$ and A being chiral.

13. The process as defined in claim 12, wherein a chiral diphosphine of the formula (III) is used, in which $R_1$ and $R_2$ represent alkyl radicals having from 1 to 10 carbon atoms, cycloalkyl radicals having from 4 to 8 cyclic carbon atoms, or aryl or alkylaryl radicals, and A is a linear or branched alkylene radical having from 1 to 10 carbon atoms, a cycloalkylene radical which has from 3 to 7 cyclic carbon atoms and is optionally substituted by 1 to 3 alkyl radicals having from 1 to 4 carbon atoms, an arylene radical or a divalent polycyclic radical, it being possible for the said radicals to be substituted by 1 or more alkoxy groups having from 1 to 4 carbon atoms, a divalent heterocyclic group having 1 or 2 heteroatoms from the group comprising oxygen and nitrogen, a linkage consisting of 1 or more divalent alkylene and/or cycloalkylene and/or heterocyclic and/or polycyclic radicals as defined above, or a linkage consisting of alkylene groups as defined above and tertiary amino groups which can be bonded directly to the phosphorus atoms via the nitrogen atom.

14. The process as defined by claim 13, wherein a diphosphine of the formula (III) is used, in which $R_1$ and $R_2$ represent an aryl radical and A is a chiral group.

15. The proces as defined by claim 11, wherein the chiral diphosphine is selected from the group consisting of tetramenthyldiphosphine, 1,2-bis-(diphenylphosphinomethyl)-cyclobutane, 4,5-bis-(diphenylphosphinomethyl)-2,2-dimethyldioxolane, 1,2-bis-(diphenylphosphinomethyl)-acenaphthene, 1,4-bis-(diphenylphosphino-2,3-dimethoxybutane and bis-(N,N'-diphenylphosphino)-bis-[N,N'-(1-phenylethyl)]-1,4-diazabutane.

16. The process as defined by claim 1, wherein the amount of rhodium complex, expressed as the number of gram atoms of rhodium per mol of diene aldehyde, is between $1 \times 10^{-4}$ and $1 \times 10^{-1}$.

17. The process as defined by claim 1, wherein the amount of phosphine, expressed as the ratio of the number of gram atoms of phosphorus to the number of gram atoms of rhodium, is such that this ratio is between 1 and 6.

18. The process as defined by claim 1, wherein the hydrogenation is carried out at a temperature of between 0° and 150° C. and under a hydrogen pressure of between 0.1 and 100 bars.

* * * * *